United States Patent [19]

Worcel et al.

[11] Patent Number: 5,437,674
[45] Date of Patent: Aug. 1, 1995

[54] OSTEOSYNTHESIS DEVICE

[76] Inventors: Alexandre Worcel, 76 Rue de Bercy, 75012-Paris; Eric Kovacs, 1 Rue Michel-Ange, 93600 - Aulnay-Sous-Bois, both of France

[21] Appl. No.: 111,548

[22] Filed: Aug. 25, 1993

[30] Foreign Application Priority Data

Aug. 25, 1992 [FR] France ................. 92 10247

[51] Int. Cl.⁶ ............. A61B 17/84; A61B 17/86
[52] U.S. Cl. .................... 606/73; 606/65; 606/66
[58] Field of Search ............ 606/72, 73, 75, 69, 606/65, 66, 67, 68; 411/38, 34, 33, 29

[56] References Cited

U.S. PATENT DOCUMENTS

| 1,320,623 | 11/1919 | Kennedy | 411/38 |
| 2,267,925 | 12/1941 | Johnston . | |
| 2,490,364 | 12/1949 | Livingston . | |
| 3,717,146 | 2/1973 | Halloran . | |
| 3,990,438 | 11/1976 | Pritchard | 606/73 |
| 4,091,806 | 5/1978 | Aginsky . | |
| 4,409,974 | 10/1983 | Freedland | 606/72 |
| 5,116,336 | 5/1992 | Frigg | 606/73 |

FOREIGN PATENT DOCUMENTS

| 0085493 | 8/1983 | European Pat. Off. . |
| 0340413 | 11/1989 | European Pat. Off. . |
| 0424734 | 5/1991 | European Pat. Off. . |
| 0468600 | 1/1992 | European Pat. Off. . |
| 2459650 | 1/1981 | France . |
| 2633345 | 12/1989 | France . |
| 2674119 | 9/1992 | France . |
| 3725111 | 2/1989 | Germany . |
| 3922044 | 2/1991 | Germany . |
| 2173565 | 10/1986 | United Kingdom . |
| WO88/03781 | 6/1988 | WIPO . |

Primary Examiner—Tamara L. Graysay
Attorney, Agent, or Firm—Oblon, Spivak, McClelland, Maier, & Neustadt

[57] ABSTRACT

A device for the holding and compression of the fragments of a fractured bone, the device including a screw whose tip is pyramidal or conical and whose body is provided, at a distal end thereof, with an outside thread, wherein the head of the screw has a plurality of foldable small wings integral with the body and wherein the screw has a device for folding the small wings. The device is useful particularly for fractures of the scaphoid, of the medial malleolus, Garden fractures 1 and 2 of the neck of the femur, pertrochanterian fractures of the femur, and generally, for fractures of small bones, and for putting in place hip or shoulder stops.

8 Claims, 8 Drawing Sheets

OSTEOSYNTHESIS DEVICE

BACKGROUND OF THE INVENTION

1. Field of the Invention

This invention relates to a device for the holding and compression of the two fragments of a fractured bone.

2. Discussion of the Background

Many devices intended to hold in compression two fragments of a fractured bone are known. U.S. Pat. No. 3,717,146 describes an intramedullary compression pin comprising threaded conical ends that are introduced into the distal and proximal fragments of the fractured bone, and which mesh with the bone tissue. U.S. Pat. No. 4,091,806 describes an intramedullary compression nail having a head in the shape of a threaded rod which sticks out from the end of one of the fragments. This head extends through a sleeve with a free end in the shape of a fork whose branches are separated by a threaded element screwed on the rod inside of the sleeve. The branches are thus driven into the walls of the medullary canal.

French patent 2,459,650 describes an intramedullary compression device able to be introduced into a hollowed-out cavity of a bone broken in two parts, a device one element of which comprises elastic elements that extend radially into the cavity and that exhibit a diameter greater than that of the cavity. These devices, which are intramedullary devices, cannot be used for epiphyseal-type fractures.

U.S. Pat. No. 3,990,438 describes a fastening and compression device for fractured bones which comprises a first part provided with cutting threads able to be anchored in the main fragment of the bone and a second threaded part to cooperate with a screw which extends on the outside of the bone and which is applied against the end of the latter to produce the axial compression. This type of screw exhibits a double drawback. On the one hand, the head of the screw does not exhibit a sufficient surface to cooperate effectively with the threading of the distal end of the screw to assure a good compression. On the other hand, in this type of screw, a bony incarceration is produced between the threads of the threaded distal part which makes the ablation of the screw very difficult.

French patent 2,633,345 describes a pin for assembly by anchoring consisting of a casing provided with several converging, sliding, expandable corollas comprising several petals ending in claws or in cutting edges. The expandable corollas, stopped by their anchoring in the interior wall of a channel, act by coming closer than by compression under the action of a screw. Such a system makes it possible effectively to hold a fractured bone in compression. However, it is fastened according to the harpoon principle, the corollas carrying the claws or the cutting edges being convergent. So long as the device is anchored in the bone by the spread claws or cutting edges, removal of the device in case of necessity cannot be performed without considerable traumatism. Considering the bony incarceration that occurs, it is not enough to proceed by unscrewing to disengage the claws or the cutting edges and remove the screw.

SUMMARY OF THE INVENTION

The invention has as its object to provide a device making possible the holding in compression of the two parts of a fractured bone, that can be used particularly for epiphyseal fractures, and providing a device that can be installed and withdrawn if necessary with a standard ancillary device without additional damage to the bone.

For this purpose, the invention has as its object a device making possible the holding in compression of the two parts of a fractured bone, consisting of a screw whose tip is pyramidal or conical and whose body is provided, at its distal end, with an outside thread, characterized in that:

the head of the screw consists of foldable small wings integral with the body; and the screw comprises means for folding the small wings.

The use of a screw according to this invention makes it possible to perform traction of the body of the screw, which puts the fracture in compression.

In a particularly advantageous embodiment, the small wings are integral with the proximal end of the body of the screw. In the unmounted state, the small wings are extended axially. When the device is put in place in a bone, the small wings are folded and form a practically flat screw head.

Preferably, the body of the screw is a hollow cylinder. The mechanism for folding the small wings can consist of an inner cylindrical element placed in the body of the screw and can undergo an axial displacement in relation to the latter, said inner element being provided with a device that can act on the free end of the small wings.

The mechanism making it possible to perform the displacement of the cylindrical element in the body of the screw can consist of threads on the inner face of the body of the screw and complementary threads on the outer face of the inner cylindrical element.

The device of this invention can be used for putting bone stops in place in hip reconstruction operations for example, and in the shoulder stops of the Latarjet type. In surgery of the spinal column, it further exhibits a great advantage for the pedicular screwing of the odontoid and in the surgical treatment of spondylolisthesis.

When the nature of the fracture necessitates putting a pin in place before putting the bone fragments under compression, the device of this invention comprises a central channel making possible passage of the pin. Such is the case for fractures of the scaphoid or navicular, fractures of the medial malleolus, hip or shoulder stops, Garden fractures 1 and 2 of the neck of the femur, pertrochanterian fractures of the femur, and generally, for fractures of small bones.

The inner cylindrical element can be a hollow cylinder or a solid cylinder.

When the device of the invention is intended to press on spongy bone, the outside thread pitch adjacent to the tip of the screw is a very wide thread pitch, known as a spongy thread pitch.

When the device is intended to press on the cortex, the outside thread pitch is a fine thread pitch, known as a cortex thread pitch.

BRIEF DESCRIPTION OF THE DRAWINGS

Various objects, features and advantages of the present invention will become more apparent from the following detailed description taken with the accompanying drawings wherein the same or similar structure is indicated by the same reference number and in which.

DESCRIPTION OF THE PREFERRED EMBODIMENTS

Figure 1:
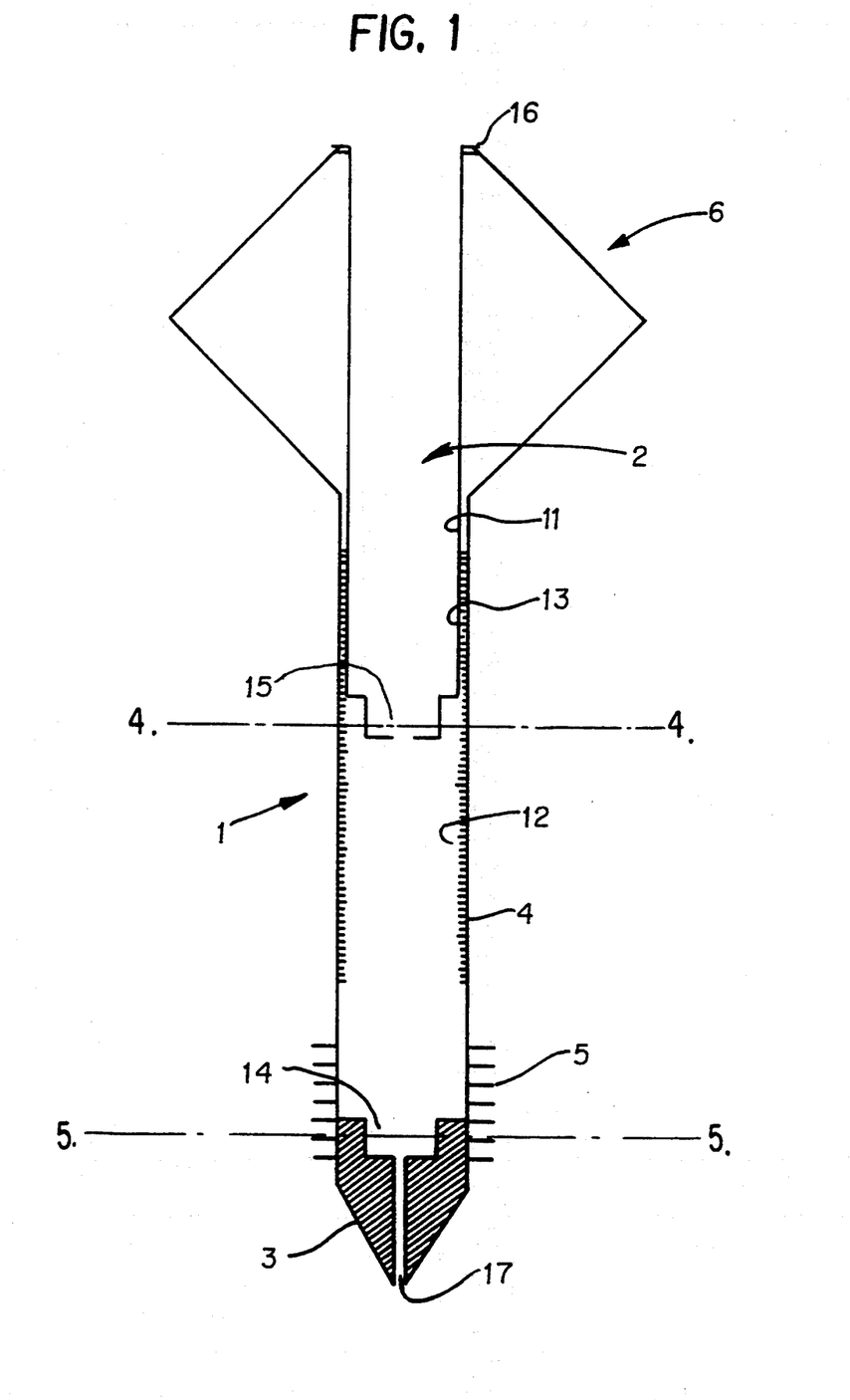
FIG. 1 represents an axial sectional view of a device according to the invention, with the small wings thereof partially folded.
Figure 2:
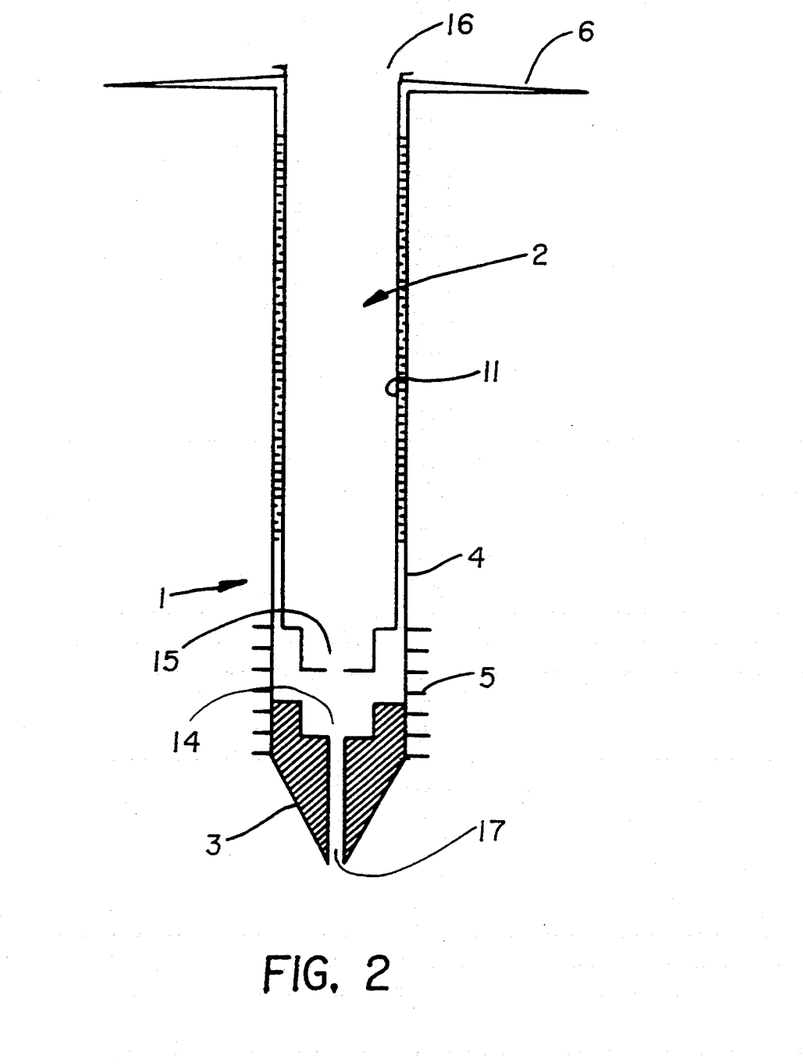
FIG. 2 represents an axial sectional view of a device according to the invention, with the small wings thereof folded.
Figure 3:
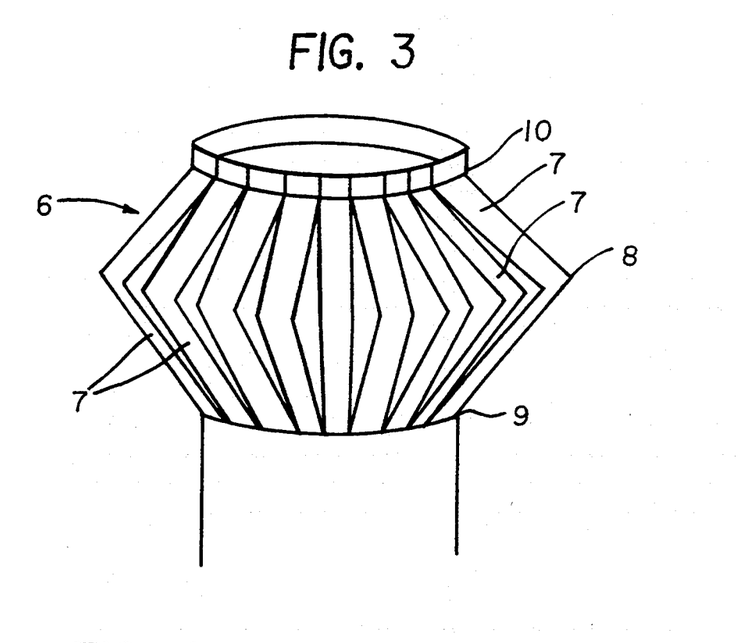
FIG. 3 is a view of the head of the screw, with the small wings thereof partially folded.

The device represented in FIGS. 1 and 2 includes a screw 1 and an inner element 2 and comprises a central channel 17. Screw 1 has a pyramidal or conical tip 3, a body 4 having an outer thread 5 at its distal end, and a head 6 having small wings 7. The detail of the head of the screw, with partially folded small wings, is represented in FIG. 3. The small wings 7 are obtained advantageously by longitudinal incisions in part of the body 4 opposite the tip 3. Foldings 8, 9 and 10 are preformed to obtain folding of the small wings in the desired direction. Screw 1 further comprises a polygon-shaped recess 14 that makes it possible to use a screwdriver to insert the screw in the cortex of the bone. Preferably, the recess is hexagonal (FIG. 5), for the use of a screwdriver with a standard hexagonal head.

Figure 7:
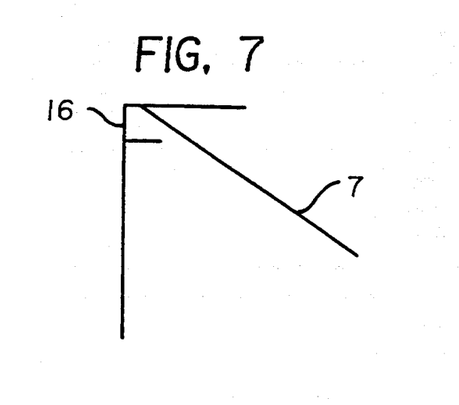
FIG. 7 is an enlarged view of flange 16.

The inner element 2 includes a hollow cylinder 11 comprising at one of its ends a flange 16 against which the free ends of small wings 7 strike.

Figure 4:
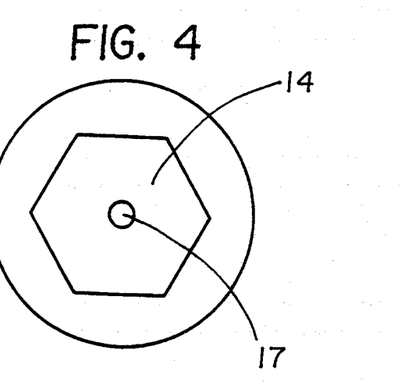
FIG. 4 is a sectional view of FIG. 1 taken along line 4—4.

Screw 1 and inner element 2 are provided with means making possible their axial relative displacement. In the embodiment shown, these means consist of a thread 12 on the inner face of screw 1 and a complementary thread 13 on the outer face of inner element 2. The threads are placed so that the small wings are elongated and so that the screwing tending to drive the inner element into the body of the screw causes the folding of the small wings. Inner element 2 has a hexagonal recess 15 in a radial plane, at its distal end, for the use of a standard screwdriver with a hexagonal head (FIG. 4). In this case, the inner element is inserted into the body of the screw after the screw is put in place in the bone. The ablation or displacement of inner element 2 produces a spreading out of the small wings due to engagement of flange 16 against the free ends of wings 7.

In a variant, in which a hollow inner cylindrical element is used, the inner face of inner element 2 can be provided with longitudinal grooves on at least a portion of its length, or with simple notches that make it possible to use a Phillips-head screwdriver to displace inner element 2 in relation to screw 1.

Figure 5:
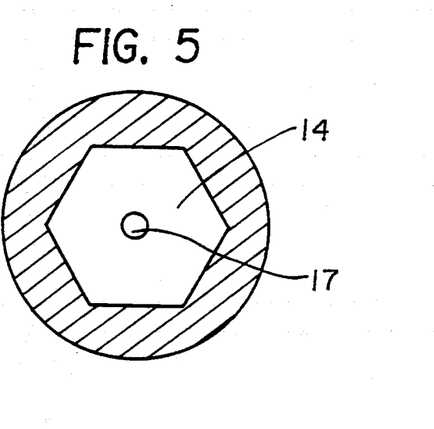
FIG. 5 is a sectional view taken along line 5—5.
Figure 6:
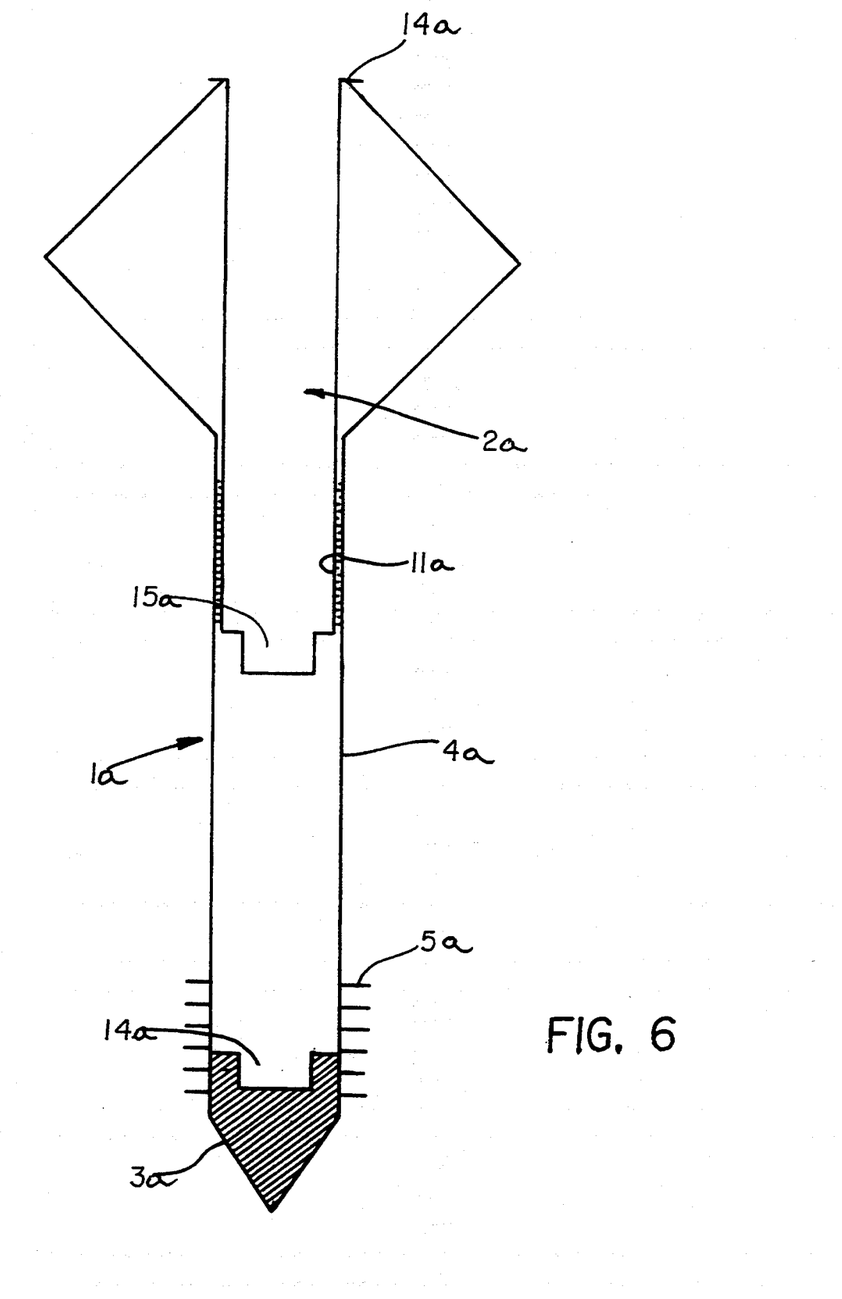
FIG. 6 is a sectional view of a device according to the invention, without a central channel.

The device represented in FIGS. 5 and 6 is a device according to this invention without a central channel. Shown here is a screw 1a, an inner element 2a, an inner thread 11a, a body 4a, an outer thread 5a, a tip 3a and an engagement member 14a.

The device according to the invention as described above can be put in place to hold in compression two fragments of a fractured bone using a simple ancillary device consisting of a tube that has a toothed distal end and a nonskid proximal handle, and a hexagonal headed screwdriver.

To install a device according to the invention, the screw selected is positioned in the tube so that only its tip projects beyond the tube, then the screwdriver is positioned in the hexagonal recess of the screw and the unit is placed on the bone surface so that the teeth of the distal end are in contact with the bone surface. The screwdriver is then temporarily withdrawn.

Advantageously, a tube is used that has a spring ratchet mechanism or any other means to prevent dropping of the screw.

An impactor can be used to strike the tube so that the teeth of the tube are locked on the bone cortex, thus preventing the displacement of the unit on the surface of the cortex. After enlarging of the entry point using a bradawl, the screwdriver upon being put back in place makes it possible to perforate the outer cortex of the bone by alternating rotary movements of the tip of the screw. When the cortex is pierced, the screw is driven in by screwing. The depth of penetration of the screw must be sufficient for outer thread 5 to be beyond the fracture line and for the base of small wings 7 to be in contact with the surface of the bone cortex. The hexagonal screwdriver and the tube are then withdrawn. Then, inner element 2 is inserted in the body of the screw by screwing, either using a Phillips-head screwdriver, or using a hexagonal head screwdriver, depending on the structure of this inner element. This operation causes the folding of the small wings and creates compression by the cooperation of thread 5 and said small wings 7.

When the nature of the fracture requires that a pin be put in place, a device according to the invention is used that has a central channel 17. A first reduction of the fracture is stabilized by a pin having a length suited to the nature of the fractured bone. A radioscopic check of the position of the pin gives the dimension of the intrabone part of the pin and makes it possible to select the size of the screw to be used. After enlargement of the entry point using a bradawl, the screw selected is positioned in the tube so that only its tip projects beyond the tube. Then, a hexagonal head screwdriver exhibiting a central channel is positioned in the hexagonal recess of the screw. The unit thus constituted is installed on the pin, so that the teeth of the distal end of the tube is in contact with the surface of the bone cortex. The screwdriver is temporarily withdrawn.

Then, the procedure is followed in the same manner as above, but withdrawing the pin at the same time as the toothed tube is accomplished.

In the particular case of the fracture of the scaphoid or navicular, the enlargement of the entry point by an auger or a hand bradawl makes possible the support of small wings 7 constituting the head of the screw on the spongy bone and no longer on the bone cortex, which prevents the projection of the head at the surface of the bone.

In the case of the stop screws, of the Latarjet type or of the hip screw type for example, the central pin is optional. The technique described above facilitates the installation of a stop and even makes possible a reduction of the dimensions of the surgical access.

Figure 8:
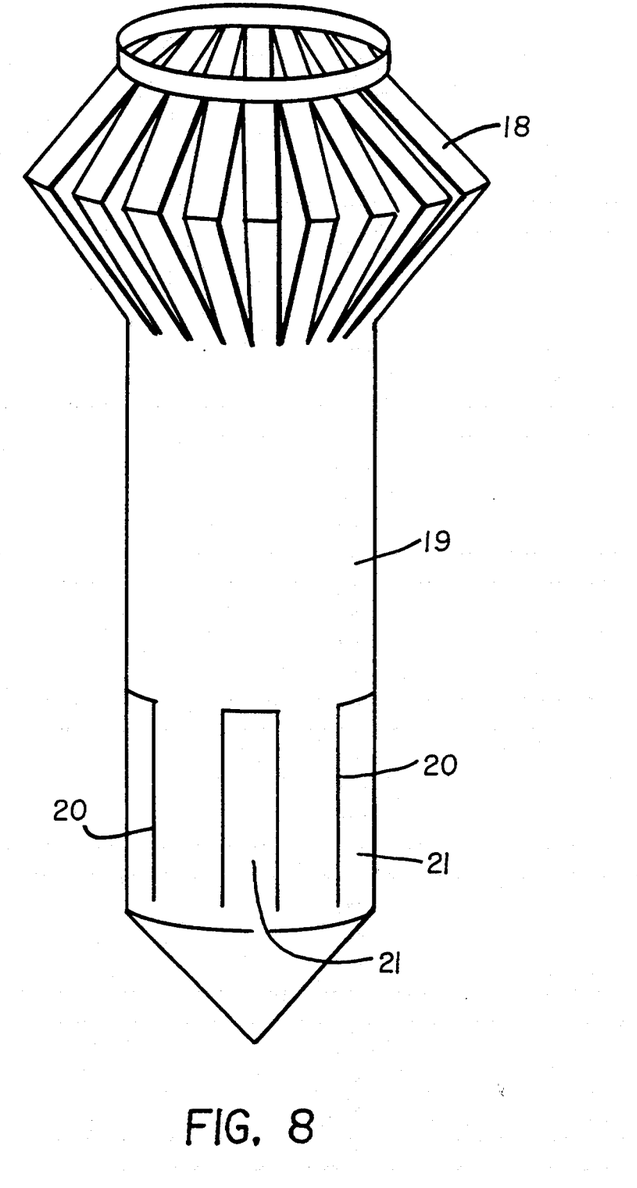
FIG. 8 represents a device comprising distal small wings before compression.
Figure 9:
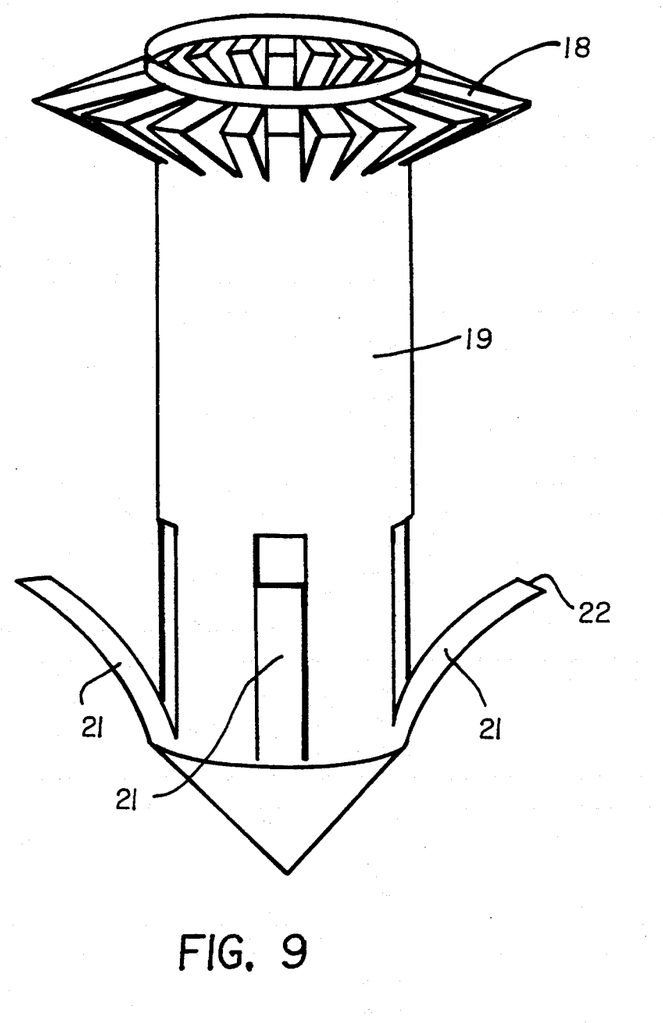
FIG. 9 represents a device having distal small wings after insertion into a bone and under compression.

FIGS. 8 and 9 represent a particular embodiment of the device of this invention in which the screw, comprising a head made of small wings 18 and a body 19, further has small wings 21 at its distal part, said small wings having a configuration such that they open like an umbrella when the distal part of the screw is put in traction by foldable small wings that constitute the head of the screw. These small wings are designated as "distal small wings." Distal small wings 21 can consist of longitudinal incisions 20 made in body 19 of the screw, said incisions creating thin strips that remain integral with the body at their end closest to the tip, and that can move away from the body at their end closest to the head, known as proximal end 22. The distal small wings exhibit a sharp edge at their proximal end 22 so that these distal small wings are separated from the body of the screw when the screw is in traction, i.e., when the small wings that constitute the head of the screw are folded (FIG. 9). In this embodiment, the outside thread located at the distal end of the screw is of a cortex-type and includes the distal small wings. In this manner, the thread does not hook the bone when the screw is put in traction, which will make possible the opening of the distal small wings 21. Of course, such a screw provided with distal small wings 21 can have a central channel for the passage of a pin.

A screw according to the invention comprising distal small wings is particularly useful for obtaining a good distal mesh while reducing the danger of tearing away. Actually, its advantage resides in the stability of the mounting performed and the elastic return effect that is created and that facilitates the uniting.

A screw of this invention having distal small wings can be installed using a standard ancillary device. It is a tube that has a toothed distal end that makes it possible to lock the tube better against the bone, and a nonskid proximal handle; a screwdriver optionally bored for the passage of a pin, the head of the screwdriver being hexagonal and its shank optionally graduated; optionally a pin having a known length (generally 13 mm); a drill bit having a diameter identical with that of the screw, a tap exhibiting a stop, having a diameter slightly greater than that of the screw, to drill the proximal cortex so as to make possible the action of the head with foldable small wings of the screw; and a flat graduated ruler to measure the part of the pin that projects beyond the bone.

For example, for uniting a pedicle, the pedicle is located, then a pin is cautiously driven in until contact with the anterior cortex of the vertebral body, while performing a radioscopic check. The part of the pin that projects beyond is measured; which makes it possible to determine the length of the screw to be used, knowing the total length of the pin. A graduated drill bit is positioned on the pin and a hole is drilled with a length 3 mm greater than the length of the screw. The proximal cortex is enlarged using an auger, then the screw provided with its screwdriver is positioned in the tube. Screwing is performed until the handle of the screwdriver is in contact with that of the tube. After having withdrawn the tube, the pin and the screwdriver, the inner cylindrical element is screwed until the small wings forming the head of the screw are completely folded, forming a flat head and causing traction on the distal part of the screw with attendant separation of the distal small wings.

The ablation of the device according to the invention with or without distal small wings can be performed without the bone being damaged. For this purpose, a simple ancillary device is used, namely the hexagonal head screwdriver used for installing the screw, or a screwdriver having as many small hooks as the screw head has small wings, which makes it possible to pull on the proximal small wings while unscrewing.

For certain applications, a device according to the invention is used in combination with a plate. Such is the case, for example, for pertrochanterian fractures of the femur.

Figure 10:
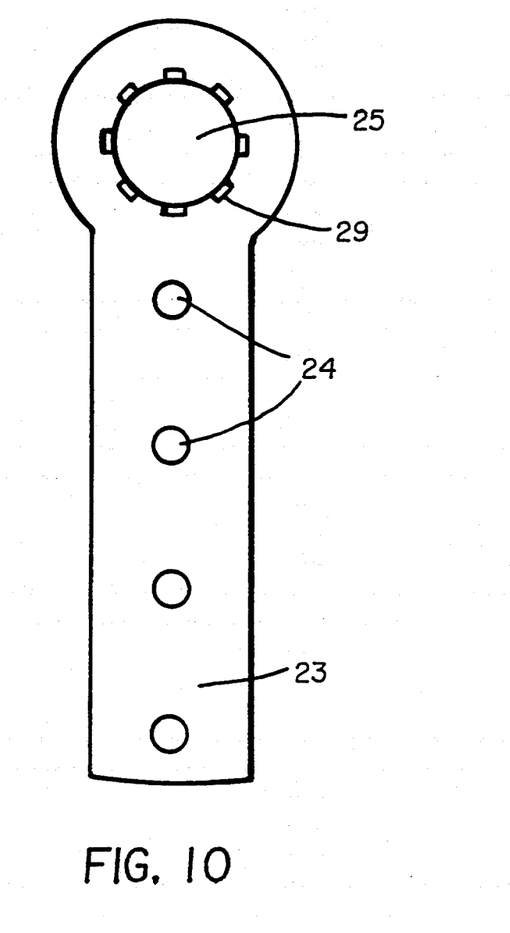
FIG. 10 represents a conventional plate as seen from above.

FIG. 10 represents a plate known in the art, as seen from above.

Figure 11:
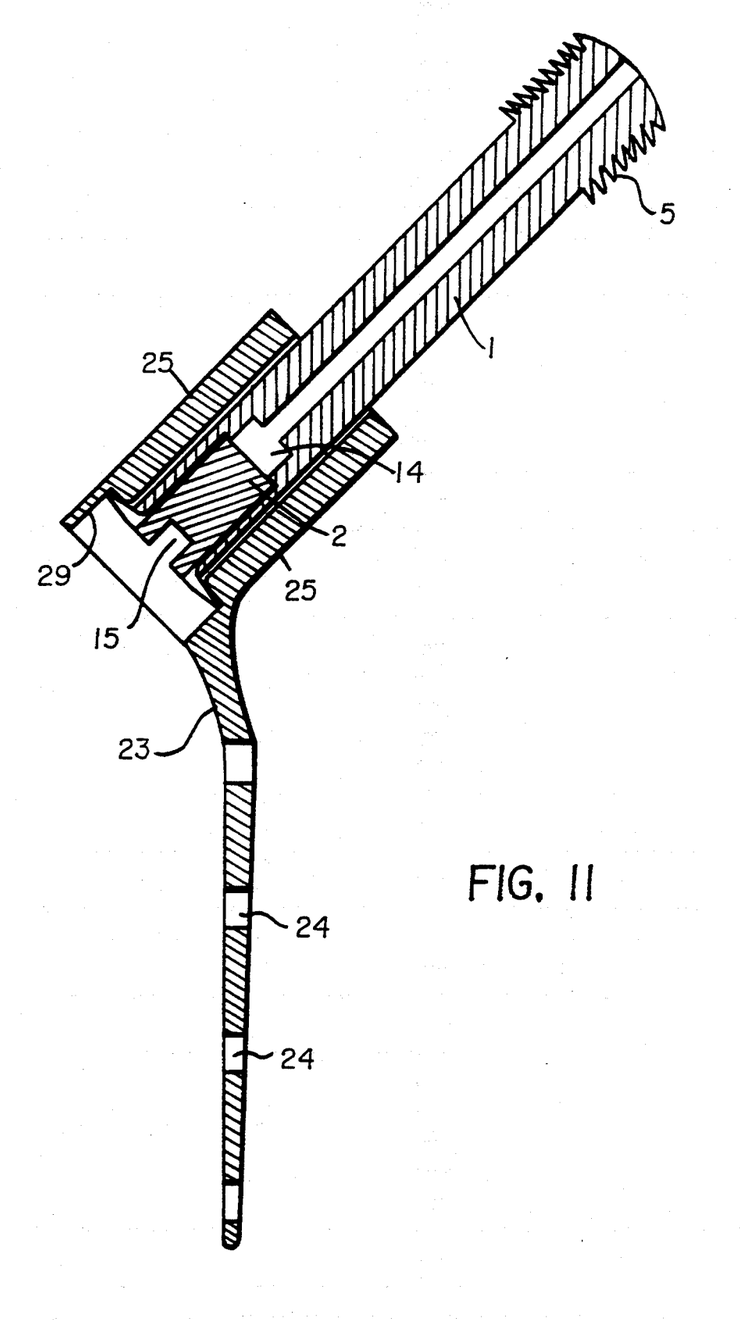
FIG. 11 represents a sagittal view of the association of a device according to this invention with a plate.

FIG. 11 represents a sagittal view of a screw-plate unit.

Plate 23 has openings 24 for the passage of standard cortex screws making it possible to fasten the plate to the bone, and a barrel 25 making it possible to engage the osteosynthesis device.

In the unit represented, a screw 1 is introduced into barrel 25. A cylindrical inner element 2 is mounted on the inside of screw 1. The distal end of screw 1 has an outer spongy thread pitch. Screw 1 has a recess 14 and the cylindrical inner element has a recess 15. The upper opening of plate 23 exhibits notches 29 in which small wings 7 are locked, which prevents rotation of the screw. The axial compression by traction is then performed by pressing on the plate.

The use of a screw with a plate makes it possible to combine two types of compression: on the one hand, compression by the weight of the body, the screw being able to slide, for example 0.5 cm, before being stopped by a ratchet mechanism; on the other hand, compression by the compression head. The device according to the invention can be used with a plate without it being necessary to provide rails or flat surfaces in the barrel of the plate, which makes it possible to make it slide better. Installing of a screw-plate unit having a device according to this invention is greatly facilitated by the fact that it is no longer necessary to finish the screwing of the cervical screw (when the device is used for a fracture of the neck of the femur or a pertrochanterian fracture, for example), which saves at least a quarter of an hour for the surgeon, this being a considerable amount of time for the patient.

The ancillary equipment necessary to install a screw-plate device comprises an oblique protractor that can be adjusted from 120° to 1400°; two augers having appropriate sizes, one that is used to prepare the passage of the screw into the bone, the other that of the barrel of the plate; a pin, a hexagonal head screwdriver and taps of successive sizes.

The screw-plate device according to the invention is installed in the following manner in the case of a fracture of the neck of the femur or a pertrochanterian fracture. After reduction of the fracture under radioscopic supervision, the pin is put in place and its position is checked under radioscopy. The housing for the screw is prepared by drilling with the small auger until 0.5 cm from the sub-chondral bone, then with the large auger at the outer cortex. The plate is put in position on its plate support, then positioned on the femur. Then the screw is screwed using a hexagonal screwdriver (optionally provided with a locking system using the interior thread of the screw) into the barrel of the plate until the small wings are locked in the notches. If compression is not desired, screwing is stopped at a mark in the barrel. Then, the pin is withdrawn and the inner cylindrical element is screwed into the screw to cause folding of the small wings.

The advantages of the device of the invention are many. In the first place, it can be installed without it being necessary previously to hollow out a cavity in the bone to be restored. It can be installed with a simple ancillary device, and withdrawn if necessary with the same ancillary device without traumatism or additional injury. Finally, when the device is put in place, and during the entire time necessary for the restoration of the fractured bone, no element sticks out of the skin provided that the head of the screw is flat.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An osteosynthesis device for holding together in compression two parts of a fractured bone comprising:
   a screw having a tip which is one of a pyramidal and conical shape and which has a body provided, at the distal end thereof, with an outside thread for engaging the bone, wherein the screw has a head which includes a plurality of foldable wings integral with the body and includes a mechanism which is engaged with said screw and the wings for folding the wings.

2. Device according to claim 1, wherein the wings are integral with a proximal end of the body of the screw.

3. Device according to claim 1, wherein the body of the screw is cylindrical and hollow.

4. Device according to claim 3, wherein the head of the screw includes axial incisions which separate adjoining wings of the plurality of wings.

5. Device according to claim 3, wherein the mechanism for folding the wings also includes an inner cylindrical element which is axially displaceable in relation to the body, and said inner cylindrical element includes a device for acting on a free end of the wings.

6. Device according to claim 5, wherein the mechanism for folding the wings comprises first threads located on the inner face of the body of the screw and the complementary threads located on the outer face of the inner cylindrical element.

7. Device according to claim 1, which comprises a cylindrical central channel having an axis corresponding to that of the body of the screw.

8. Device according to claim 1, which comprises a plate which includes a barrel in which the screw is inserted.

* * * * *